United States Patent [19]

Hoffmann et al.

[11] Patent Number: 5,525,389
[45] Date of Patent: * Jun. 11, 1996

[54] SELF-ADHESIVE LAMINATE FOR NAILS

[75] Inventors: Hans-Rainer Hoffmann; Reinhard von Kleinsorgen, both of Neuwied; Günter Simon, Hillesheim; Dorothea Steinborn, Neuwied, all of Germany

[73] Assignee: LTS Lohmann Therapie-Systeme GmbH & Co. KG, Neuwied, Germany

[*] Notice: The term of this patent shall not extend beyond the expiration date of Pat. No. 5,415,903.

[21] Appl. No.: 299,337

[22] Filed: Aug. 31, 1994

Related U.S. Application Data

[63] Continuation of Ser. No. 969,145, filed as PCT/EP91/01402 Jul. 26, 1991 published as WO92/02264 Feb. 20, 1992, abandoned.

[30] Foreign Application Priority Data

Jul. 30, 1990 [DE] Germany ............... 40 24 125.4

[51] Int. Cl.⁶ ..................................... C09J 7/02
[52] U.S. Cl. .................. 428/41.5; 132/73; 132/285
[58] Field of Search ............... 428/40, 42; 132/73, 132/285

[56] References Cited

U.S. PATENT DOCUMENTS

| | | | |
|---|---|---|---|
| 2,288,386 | 6/1942 | Belden | 132/73 |
| 2,746,460 | 5/1956 | Jellinek | 132/73 |
| 2,764,166 | 9/1956 | Bogoslowsky | |
| 2,864,384 | 12/1958 | Walter | 132/73 |
| 2,979,061 | 4/1961 | Greenman | 132/73 |
| 4,682,612 | 7/1987 | Giuliano | |
| 4,824,702 | 4/1989 | Straub | 132/73 |
| 4,876,121 | 10/1989 | Cohen | |
| 4,903,840 | 2/1990 | So | 428/76 |
| 4,947,876 | 8/1990 | Larsen | 132/73 |
| 4,957,730 | 9/1990 | Bohn et al. | |
| 5,044,384 | 9/1991 | Hokama | 132/73 |
| 5,225,185 | 7/1993 | Castrogiovanni | |
| 5,415,903 | 5/1995 | Hoffman | 428/15 |

FOREIGN PATENT DOCUMENTS

| | | |
|---|---|---|
| 2362818 | 6/1974 | Germany |
| 3337458 | 4/1985 | Germany |
| 340592 | 10/1959 | Switzerland |

*Primary Examiner*—Jenna L. Davis
*Attorney, Agent, or Firm*—Collard & Roe

[57] ABSTRACT

The invention relates to a self-adhesive, plasticizer-containing laminate consisting of a) a film-forming polymeric layer containing dyestuffs and/or pigments, b) a pressure-sensitive adhesive layer, and c) a removable, preferably siliconized protective film covering the pressure-sensitive adhesive layer, the film-forming polymeric layer a) of which is at least entirely covered by a layer being resistant towards the other components of the laminate and towards the materials used in the production of the laminate. The invention further relates to the use of said laminate as artificial nails applicable to toenails or fingernails.

19 Claims, 1 Drawing Sheet

SELF-ADHESIVE LAMINATE FOR NAILS

This is a continuation of application Ser. No. 07/969,145 filed on Jan. 28, 1993, now abandoned which is the U.S. national stage of International Application PCT/EP91/01402 filed on Jul. 26, 1991 and which designated the U.S.

DESCRIPTION

The present invention relates to a self-adhesive laminate which contains at least one plasticizer, may be shaped to toenails and/or fingernails, and consists of a) a film-forming polymeric layer containing dyestuffs and/or pigments, b) a pressure-sensitive adhesive layer, and c) a removable, preferably siliconized protective film covering the pressure-sensitive adhesive layer.

The present invention further relates to a process for the production of said laminate as well as to the use thereof as artificial nails applicable to toenails or fingernails, respectively. It is known to treat nails with solvent-containing polymer lacquers to achieve a cosmetic effect (nail lacquer). It is also known to add an antimycotic substance or a preservative agent to such a lacquer. It is also common knowledge that applying such a nail lacquer and achieving the desired appearance requires considerable care (time involved, drying of the lacquer, practice, appearance). In view of the enormous worldwide consumption of organic solvents the content thereof in the known nail lacquers means a considerable environmental pollution which should be eliminated or at least reduced for reasons of environmental protection. For this reason alone the use of decorative films for application on nails connected with the properties demanded by the consumer, such as Gloss and color, durability, wearability, and natural appearance, should be recognized as a suitable substitute for solvent-containing lacquers. The use of artificial nails, which are connected to the nail in various manners, is known. It is known by DE-OS 23 62 818 to paste over nails with an adhesive film of PVC. However, such a system was not accepted by the consumer, since PVC used as polymeric material does not meet the requirements with respect to luster, hardness, flexibility, and durability. The high ultimate strength of PVC-films and similar polymeric films, such as polyethylene, polypropylene, or polyester, make it more difficult to shape the film to the nail by simple shearing, and, in addition, involve the risk of injuring the nail bed. Formability to the nails as well as stability with respect to applicability are directly connected with the brittleness of the laminate. In this connection, it was noticed that the ideal properties of a nail lacquer laminate (laminate on the basis of nitrocellulose— available nail lacquer) involve problems with respect to stability, i.e., the laminate becomes brittle (dries up) during storage and therefore cannot be applied any longer.

It was accordingly the object of the present invention to develop a self-adhesive laminate which is similar to the commercially available, solvent-based nail lacquers and meets consumers' requirements with respect to gloss, surface hardness, flexibility, durability on the nail without a foreign-body sensation, which can be formed to the nail and, combined with the aforementioned properties, exhibits sufficient stability against drying-up and the high brittleness involved. It turned out to be difficult to achieve this objective, in particular with respect to combining sufficient stability with simultaneous sufficient surface hardness and flexibility, since these properties are contrary to each other. If a stable laminate is obtained, the surface hardness thereof is insufficient due to the high amount of plasticizers. If the surface hardness suffices, the laminate becomes brittle during storage so fast that the application thereof is rendered impossible due to breakage of the laminate.

Most surprisingly, it has been found that the combination of these essential properties may be achieved, if a lacquer, preferably a lacquer based on nitrocellulose and/or acrylate, is applied on a covering film first, then the lacquer dried under solvent recovery, and this combination laminated with an adhesive film and a protective layer. Thus, the subject matter of the present invention is a self-adhesive laminate containing at least one plasticizer and being formable to toenails and/or fingernails, and consisting of a) a film-forming polymeric layer containing colorants and/or pigments, b) a pressure-sensitive adhesive layer, and c) a removable protective film which preferably is siliconized and covers the pressure-sensitive adhesive layer which laminate is characterized in that at least the entire area of the film-forming polymeric layer is covered by a removable layer being resistant towards the other components of the laminate and towards the materials used in the production of the laminate. Coating the lacquer (i.e., the polymeric layer) on the covering layer, which is to be removed prior to application, on the one hand, permits that the surface of the polymer layer may be structured, and, on the other hand, ensures stability and utility of the laminate up to application thereof. The superficial structure of the polymeric layer corresponds to a negative print. The size of the covering layer at least corresponds to the size of the laminate to be coated, it is preferably larger than that. The covering layer may consist of a film, preferably a plastic film, a paper, or a textile fabric. The covering layer advantageously consists of a transparent material. The cover layer may be single- or multi-layered.

The side of the covering layer being coated with the polymeric layer is preferably rendered adhesive, i.e., the adhesion between covering layer and laminate is less than the adhesion between adhesive layer and protective film. Advantageously, the covering layer is provided with a peel-off aid facilitating the handling. The adhesive layer of the laminate may consist of a known adhesive mass. The area weight of the adhesive layer is in the range of 20 to 100 g/m$^2$, it preferably amounts to approximately 25 to 75 g/m$^2$.

The polymeric layer of the laminate exhibts a thickness of 25 to 200, preferably 60 to 150 μm; said polymeric layer may also have a single- or multi-layer structure, in case of a multi-layer structure the individual layers may be of different compositions.

The portion of plasticizer within the polymer layer (the adhesive layer may as well contain the same or a different softener) amounts to 1 to 30, preferably 5 to 12.5, and in particular preferred 7 to 10%-wt., relative to the polymers and, if present, pigments of the lacquer or the adhesive matrix, respectively.

Citric acid esters are preferably used as softeners. In addition, camphor may be present as softener. The addition of camphor causes the film to aftercure after application by evaporation of the camphor. Loss of camphor prior to application is avoided by the covering layer.

The polymeric layer/s advantageously contain or consist of nitrocellulose alone, acrylates alone, or mixtures of these two components which are originally known for the use in nail lacquers.

Additives, such as odour-active components and/or active substances, may be added to the polymeric layer and/or the adhesive layer; these active substances preferably are antimycotically effective substances, such as clotrimazole, miconazole, ketoconazole, naftifin, ciclopiroxolamine, fenticlor, sulbentine, tolnaftate, and haloprogin. In addition, the adhesive layer may contain an agent promoting the penetration of the active substance into the nail. The addition of penetration accelerators or penetration enhancers to an active substance/adhesive formulation is known from the transdermal therapeutic systems. Substances promoting the active substance transport into or through the skin, respectively, for example, are dimethyl sulfoxide (DMSO) and dimethyl formamide (DMF), as well as a large number of various emulsifiers, fatty acids and the esters thereof.

A further subject matter of the present invention is a method for the production of the self-adhesive laminates, which method is characterized in that a lacquer containing dyes and/or pigments, at least one plasticizer, and at least one film-forming polymer being dissolved in an organic solvent, is applied on a removable covering layer having at least the same size as the laminate, the lacquer is dried under solvent recovery, and the lacquer-coated side of the covering layer, which is coated with the dried lacquer, is laminated with an adhesive film and a protective layer.

The present invention displays the following advantages: No organic solvent is released to the environment. The laminates according to the present invention which are suitable as artificial toenails or fingernails meet the requirements demanded by the consumer with respect to gloss, hardness, flexibility, and durability, and they prevent injuries of the nail bed. In addition, the polymeric layer may be provided with a structure for decorative purposes by using an accordingly structured covering layer. Finally, the present invention is also directed to the use of the laminates according to the present invention as artificial toenails or fingernails.

The present invention will be explained by the following example which is to be understood as illustrative only and not in a limiting sense.

EXAMPLE:

1. An adhesive mass containing same quantities of polyisobutylene solid, aliphatic hydrocarbon resin hydrogenated resin of colophony 0.01 part of stabilizer (antioxidant)

0.05 part of plasticizer (citric acid ester)

10 parts of special purpose benzine is applied on a polyester film one side of which is rendered abhesive; it is then dried (thickness of adhesive layer: 80 μm).

(laminate 1)

1. Adhesive mass:

| | |
|---|---|
| 0.05 kg | plasticizer |
| 0.153 kg | polyisobutylene (mean molecular weight approximately 900,000 to 1,400,000) |
| 0.137 kg | solid, aliphatic hydrocarbon resin |
| 0.137 kg | hydrogenated colophony resin |
| 0.005 kg | stabilizer (antioxidant) |
| 1.148 kg | special purpose benzine 80–110 as solvent |

2. A commercially available nail lacquer mass consisting of

| | |
|---|---|
| 4 | parts of cellulose nitrate |
| 1 | part of acrylate copolymer |
| 1 | part of sulfonamide resin |
| 0.1 | part of camphor |
| 1 | part of plasticizer (citric acid ester) |
| 3 | parts of coloring pigment |
| 30 | parts of solvent | is applied on the covering layer (polyester film 50 μm) and dried (thickness of polymeric layer 200 μm)

| | |
|---|---|
| 136.5 g | nitrocellulose |
| 73.5 g | butanol |
| 50.0 g | toluene sulfonamide resin (Santolite) |
| 50.0 g | polyacrylic ester (Acronal) |
| 30.0 g | camphor |
| 23.0 g | plasticizer (citric acid ester) |
| 60.0 g | dibutyl phthalate |
| 100 g | butylacetate |
| 200 g | ethyl acetate |
| 200 g | toluene |
| 77 g | ethanol |
| 1000 g | |
| 20 g | coloring pigments |

(laminate 2)

Nitrocellulose: film former (rigid polymer)
Polyacrylic ester: film former (plasticized polymer)
Sulfonamide resin: luster intensifier 3. Laminates 1 and 2 are then laminated on top of each other in such a way that the adhesive layer and the polymeric layer are connected with each other.

(laminate 3)

4. A siliconized and aluminized polyester film (protective layer) is provided with semi-circular cuts (peel-off aid).

(Full punching through the film—FIG. 4)

5. The laminate 3 is laminated on the protective layer according to 4.; prior to this, the polyester film of laminate 1 is removed from laminate 3 so that the adhesive layer is lying on top of the protective layer.

6. The covering layer of the laminate so obtained is punched into portions, without punching through the protective layer. The sizes of said portions approximately correspond to those of different fingernails. The partitioning inserts between said portions are separated by lattice.

7. The laminate obtained by step 6. is divided by cutting, this being done in such a way that laminate-supports (in the following called supports) are obtained which at least exhibit 10 portions.

(one portion each for a fingernail of two hands)

The laminate so produced was stable after storage for 6 months at 50° C. and met the required application and wearing properties. Products without covering layer become brittle after two days of storage at 50° C. and cannot be applied any longer. The laminates produced according to the above example are applied to the nail as follows: To treat a nail, one portion is removed from the protective layer by means of the peel-off aid and glued on the nail. Subsequently to or simultaneously with glueing, the covering layer is removed, and the self-adhesive polymer layer then shaped to the nail. If the covering layer covers several portions at the same time, it is removed for a short moment in order to release the self-adhesive polymer layer from the protective layer.

After application, the self-adhesive polymer layer exhibits the same wearing properties as the lacquer layer applied by a solvent-containing nail lacquer mass; however, in contrast to glueing so-called artificial fingernails, there is no sensation of a foreign body.

The self-adhesive polymeric layer is removed from a nail by applying to said polymeric layer a projecting pressure sensitive film, the film is then pressed at the edges of the polymeric layer and the latter is entirely peeled off the nail. (Removal of price labels on packages by means of a pressure sensitive adhesive tape).

There is no adhesive residue of the self-adhesive polymer layer on the nail; cleaning the nail with an organic solvent thus becomes unnecessary.

This application system (laminate) also prevents the so-called "staining" (penetration of colorant into the nail) frequently occurring when conventional nail lacquers are used.

The invention will be further illustrated by the accompanying drawings.

Figure 1:
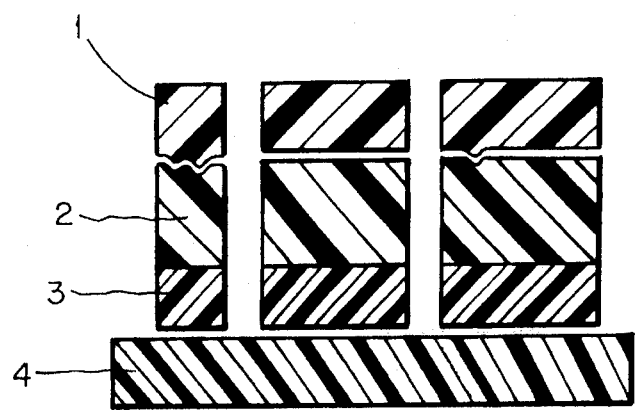
FIG. 1 is a cross-section of a support with three sections

Referring to FIG. 1, the covering layer 1 (polyester film having a thickness of 100 μm, with partly structured surface, to be removed prior to application) is provided with a polymeric layer 2 (nail lacquer based on nitrocellulose, pigmented, layer thickness 200 μm), and on said polymeric layer an adhesive layer 3 is positioned (based on polyisobutylene, thickness 80 μm). The laminate is completed by a protective layer 4.

Figure 2:
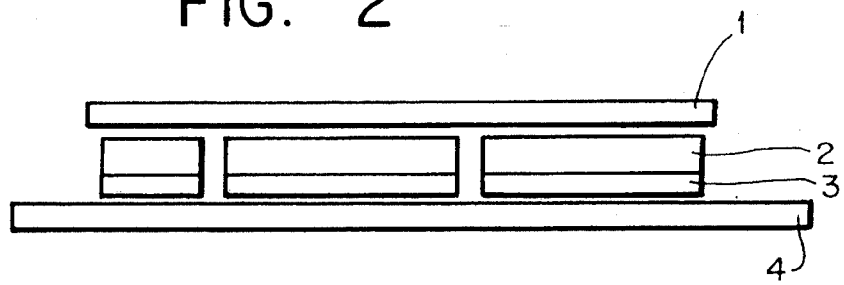
FIG. 2 shows a covering layer covering several portions at the same time

FIG. 2 shows a covering layer 1 covering several sections.

Figure 3:
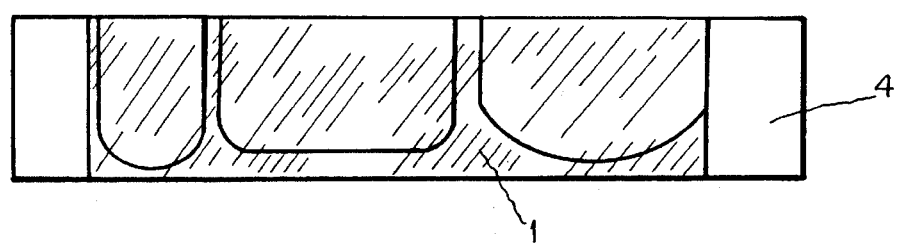
FIG. 3 shows a plan view on three sections being covered by the covering layer

FIG. 3 shows the plan view on three sections covered by the covering layer.

Figure 4:
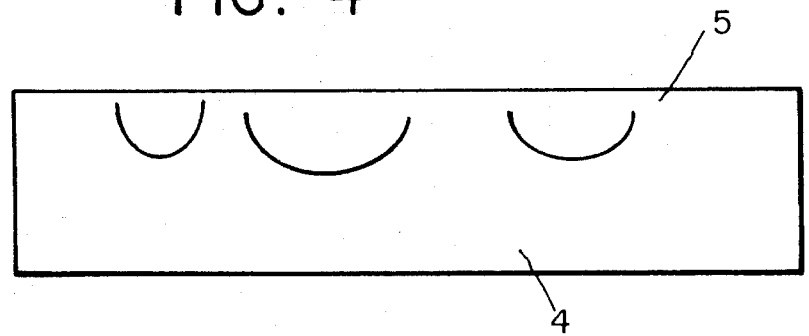
FIG. 4 shows the back side of the protective layer with punched peel-off aid.

FIG. 4 shows the back side of the protective layer 4 with punched peel-off aid 5.

It is understood that the specification and examples are illustrative but not limitative of the present invention and that other embodiments within the spirit and scope of the invention will suggest themselves to those skilled in the art.

We claim:

1. A self-adhesive laminate containing at least one plasticizer and being formable to toenails or fingernails, comprising:

a) a film-forming polymeric layer containing said at least one plasticizer, dyestuff, pigment or mixture thereof;

b) a pressure-sensitive adhesive layer located thereon; and c) a removable protective film covering the pressure-sensitive adhesive layer, wherein the film-forming polymeric layer is, on its reverse side, covered by a detachable covering film being resistant toward the other components of the laminate and toward the materials used in the production of the laminate, wherein the covering film is provided with an adhesive coating, wherein the adhesion of the covering film to the polymeric layer is less than the adhesion between the adhesive layer and the protective film, and wherein the polymeric layer contains a substance selected from the group consisting of nitrocellulose, acrylates, and mixtures thereof, wherein the acrylates are polymers selected from the group derived from acrylic acid, dimethylaminoethyl methacrylate, methyl acrylic acid and mixtures thereof.

2. The self-adhesive laminate according to claim 1, wherein the covering film consists of a plastic material.

3. The self-adhesive laminate according to claim 1, wherein the covering film is provided with a peel-off aid.

4. The self-adhesive laminate according to claim 1, containing citric acid as plasticizer.

5. The self-adhesive laminate according to claim 4, containing camphor as plasticizing agent.

6. The self-adhesive laminate according to claim 1, wherein the concentration of said at least one plasticizer within the polymeric layer ranges from 1 to 30%-wt., relative to the polymers of the layer or layers.

7. The self-adhesive laminate according to claim 1, wherein the polymeric layer or the adhesive layer or both contain an odor-active component.

8. The self-adhesive laminate according to claim 1, wherein the adhesive layer or the polymeric layer or both comprises an antimycotically effective substance.

9. The self-adhesive laminate according to claim 8, wherein the adhesive layer or polymeric layer or both comprises as an antimycotic at least one active substance selected from the group consisting of clotrimazone, miconazole, ketoconazole, econazole, naftifin, ciclopiroxolamine, fenticlor, sulbetine, tolnaftate, and haloprogin.

10. The self-adhesive laminate according to claim 1, wherein the adhesive layer comprises a component promoting the penetration of the active substance into the nail.

11. The self-adhesive laminate according to claim 1, wherein the area weight of the adhesive amounts to 20 to 100 g/m².

12. The self-adhesive laminate according to claim 1, wherein the polymeric layer has a thickness of 25 to 200 μm.

13. The self-adhesive laminate according to claim 1, wherein the polymeric layers are of different compositions.

14. The self-adhesive laminate according to claim 1, wherein the protective film is a siliconized protective film.

15. The self-adhesive laminate according to claim 6, wherein the concentration of said at least one at least one plasticizer within the polymer layer ranges from 5% to 12.5%-wt.

16. The self-adhesive laminate according to claim 15, wherein the concentration of said at least one at least one plasticizer within the polymer layer ranges from 7% to 10%-wt.

17. The self-adhesive laminate according to claim 10, wherein the component promoting the penetration of the active substance into the nail is selected from the group consisting of DMSO and DMF.

18. The self-adhesive laminate according to claim 11, wherein the area weight of the adhesive ranges from 25 to 75 g/m².

19. The self-adhesive laminate according to claim 12, wherein the polymeric layer has a thickness of 60 to 150 μm.

* * * * *